United States Patent [19]

Kollmeyer

[11] Patent Number: 4,626,543

[45] Date of Patent: Dec. 2, 1986

[54] INSECTICIDAL 2,6-DIFLUOROBENZOYL DERIVATIVES OF 4-SUBSTITUTED-1,3-THIAZOLE-2-ACETONITRILES

[75] Inventor: Willy D. Kollmeyer, Modesto, Calif.

[73] Assignee: Shell Oil Company, Houston, Tex.

[21] Appl. No.: 697,546

[22] Filed: Feb. 1, 1985

[51] Int. Cl.[4] .................... C07D 277/30; A01N 43/78
[52] U.S. Cl. ...................................... 514/365; 548/204
[58] Field of Search .................... 548/204; 514/90, 365

[56] References Cited

U.S. PATENT DOCUMENTS

| | | | |
|---|---|---|---|
| 4,153,705 | 5/1979 | Puttner et al. | 424/270 |
| 4,297,361 | 10/1981 | Puttner et al. | 424/263 |
| 4,320,125 | 3/1982 | Puttner et al. | 424/248.51 |
| 4,371,734 | 2/1983 | Seybold | 544/300 |

Primary Examiner—Robert Gerstl

[57] ABSTRACT

Compounds of the formulas I, II, or III

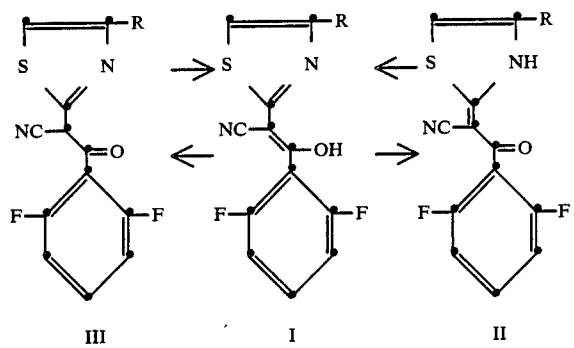

wherein R is an alkyl group containing 2 to 6 carbon atoms optionally substituted by one or more halogen atoms, a cycloalkyl group containing 3 to 6 ring carbon atoms optionally substituted by one of more alkyl groups containing 1 or 2 carbon atoms, an aryl or aralkyl group containing 6 to 10 carbon atoms optionally ring-substituted by one or more halogen atoms or alkyl groups containing 1 or 2 carbon atoms or an alkoxycarbonyl alkyl group in which the alkyl portions contain from 1 to 6 carbon atoms, are useful as insecticides, particularly against the species of the Order Lepidoptera.

9 Claims, No Drawings

INSECTICIDAL 2,6-DIFLUOROBENZOYL DERIVATIVES OF 4-SUBSTITUTED-1,3-THIAZOLE-2-ACETONITRILES

BACKGROUND OF THE INVENTION

1. Field of the Invention

The present invention relates to novel 2,6-difluorobenzoyl derivatives of 4-substituted-1,3-thiazole-2-acetonitriles, their use as insecticides and to insecticidal compositions containing the novel derivatives.

2. Description of the Prior Art

From U.S. Pat. Nos. 4,153,705, 4,297,361 and 4,320,125 it is known that certain benzoyl 1,3-thiazole-2-acetonitriles are useful as insecticides. However, there continues to be a need for new insecticides, particularly ones effective against Lepidoptera species.

SUMMARY OF THE INVENTION

The present invention is directed to new compounds which are 2,6-difluorobenzoyl derivatives of 4-substituted-1,3-thiazole-2-acetonitriles having the formulas I, II or III,

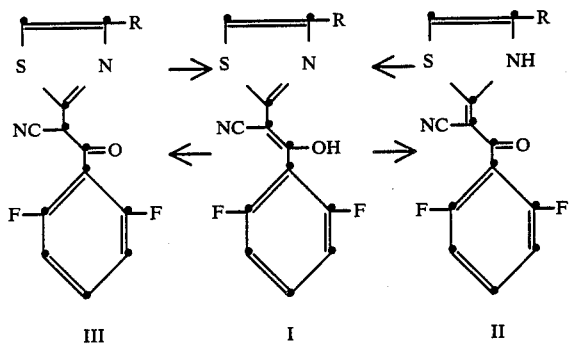

wherein R is an alkyl group containing 2 to 6 carbon atoms optionally substituted by one or more halogen atoms, a cycloalkyl group containing 3 to 6 ring carbon atoms optionally substituted by one or more alkyl groups containing 1 or 2 carbon atoms, an aryl or aralkyl group containing 6 to 10 carbon atoms optionally ring-substituted by one or more halogen atoms or alkyl groups containing 1 or 2 carbon atoms or an alkoxycarbonylalkyl group in which the alkyl portions contain from 1 to 6 carbon atoms. The compounds are useful as insecticides, particularly against the species of the Order Lepidoptera.

The compounds of formulas I, II or III of the invention are prepared by treating an appropriate 4-substituted-1,3-thiazole-2-acetonitrile in which the 4-substituent is a group R, defined in formula I, II or III, with 2,6-difluorobenzoyl chloride in the presence of base. The compounds I, II and III are tautomers. The spectral properties of both solids or solutions are consistent with tautomer I.

The 4-substituted-1,3-thiazole-2-acetonitriles are prepared by cyclization of the monothioamide derived from malononitrile, i.e. $NH_2-C(S)CH_2CN$, with the appropriately substituted halomethyl ketone, i.e. $RC(O)CH_2Hal$ in which R is defined as for formulas I, II or III and Hal is halogen, preferably bromine or chlorine, in the presence of a base, such as ethanolic potassium hydroxide.

The appropriately substituted halomethyl ketones are generally known in the art and preparable by conventional procedures known in the art. Some of the chloromethyl ketones are also commercially available. The bromomethyl ketones are prepared by bromination of the appropriately substituted methyl ketones with $Br_2$ in a suitable medium, such as methylene chloride, diethyl ether or acetic acid, eg. according to the method of J. H. Boyer and D. Straw, J. Am. Chem. Soc., 74, 4506 (1952).

The appropriately substituted methyl ketones are generally known in the art and preparable by conventional procedures known in the art. Some are even commercially available, e.g. pinacolone, o-methylacetophenone and acetophenone. For example, the methyl ketones are prepared by (a) treating an acyl chloride, RC(O)Cl in which R is defined as in formulas I, II or III, with diethyl malonate in the presence of alcoholic magnesium and absolute ether followed by treating the resulting product with aqueous acetic acid or sulfuric acid e.g. according to the method of H. G. Walker and C. R. Hauser, J. Am. Chem. Soc., 68, 1386 (1946) or by (b) treating an alpha-bromoisobutyric acid ester with zinc metal, mercuric chloride and acetic anhydride, e.g. according to the method of I. I. Lapkin and U. V. Fotin, J. Org. Chem. USSR, 11, 2360 (1975). The alkyl alpha-bromoisobutyric acid esters are prepared from isobutyric acid by alpha-bromination, followed by conventional esterification techniques known in the art.

Non-limiting illustrations of the species of the invention include the specific compounds of formulas I, II or III wherein R is ethyl, propyl, isopropyl, butyl, isobutyl, secondary-butyl, cyclobutyl, 1-methylcyclobutyl, cyclopentyl, cyclohexyl, 2,6-dimethylphenyl, 2,4,6-trimethylphenyl, 2-chlorophenyl, 2,4-dichlorophenyl, 2,6-dichlorophenyl, 2,6-difluorophenyl, or 2-fluorophenyl and the like.

ILLUSTRATIVE EMBODIMENTS

The invention is illustrated by the following embodiments, which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

Embodiment 1

2-Cyanothioacetamide

The Procedure of U.S. Pat. No. 2,733,260 was employed. Thus, a stirred solution of 66.0 g malononitrile and 15.0 g triethanolamine in 180 ml of ethanol was treated with gaseous hydrogen sulfide, introduced via a fritted glass sparging tube. The mixture gradually warmed to ca 45° C., and after 2 hrs, slightly more than one equivalent of $H_2S$ had been added. Then the mixture was cooled by an ice-bath. The resultant precipitate was isolated by filtration and recrystallized from ethanol to give 65.49 g of the desired product as a tan solid, m.p. 118°-120° C. (lit m.p. 121°-123° C.).

Embodiment 2

3,3-Dimethyl-2-pentanone

A solution of 75.0 g of 2,2-dimethylbutyric acid in 60 ml thionyl chloride was heated at 80° C. overnight.

Excess thionyl chloride was removed by rotary evaporation, and the remaining residue was distilled to yield 76.72 g of 2,2-dimethylbutanoyl chloride as a colorless oil, b.p. 45° C. (50 mm Hg), which was stored at ambient temperature until used as below.

Magnesium shavings (15.24 g) were treated with 14.09 ml of absolute ethanol and 1.41 ml of carbon tetrachloride. The reaction, which started almost immediately, was allowed to proceed for a few minutes and 200 ml of absolute ether was then added cautiously. To the resulting mixture was added a solution of 99.30 g of diethyl malonate in 56 ml absolute ethanol and 70 ml absolute ether at such a rate that rapid refluxing was maintained, heat being applied when necessary. After addition was complete, the mixture was refluxed for one-half hour, or until the magnesium had dissolved. To the clear solution was added with vigorous stirring, an ethereal solution of 76.72 g of the above 2,2-dimethylbutanoyl chloride, and the mixture was refluxed for one-half hour. The reaction mixture was cooled, acidified with dilute sulfuric acid, and extracted with ether. The combined extracts were washed with water, dried (MgSO$_4$) and distilled to give 145.0 g of a yellow oil. This entire amount was refluxed overnight in a solution of 14 ml concentrated sulfuric acid, 80 ml of water and 120 ml of acetic acid. The reaction solution was cooled in an ice bath, made alkaline with 20% sodium hydroxide solution, and extracted with several portions of ether. The combined ether extract was washed with water, brine, dried (Mg SO$_4$), and stripped to give a yellow oil. Distillation yielded 34.44 g of the desired product as a colorless oil, b.p. 52°–53° C. (50 mm Hg).

Embodiments 3–4

Following procedures similar to those described in Embodiment 2 above, the following methyl ketones were prepared.

TABLE 1

METHYL KETONES $$R-\overset{O}{\underset{\|}{C}}-CH_3$$

| Embodiment | R | b.p. °C., (mm Hg) |
|---|---|---|
| 3 | 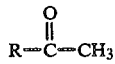 | 40 (30) |
| 4 | —C(CH$_3$)$_2$CH$_2$Cl | not determined |

Embodiment 5

Methyl 2,2-Dimethyl-3-oxobutanoate

To a mixture of 20.86 g of 20 mesh zinc metal, 165 ml of 120:210 by volumes ether:benzene and 0.05 g of mercuric chloride was added a few drops of a solution of 26.64 g of methyl alpha-bromoisobutyrate and 18.72 g of acetic anhydride followed by brief heating with a heat gun to initiate the reaction. The remaining solution was added slowly at reflux. After addition was complete, the mixture was refluxed for 2½ hrs, cooled, poured over 12 ml concentrated HCl mixed with ice, and extracted with ether. The combined extract was washed with water, dried (MgSO$_4$) and stripped to give 23.15 g of a yellow oil. Distillation yielded 15.41 g of the desired product as a colorless oil, b.p. 32° C. (1 mm Hg).

Embodiment 6–7

Following procedures similar to those described in Embodiment 5, the following methyl ketones were prepared.

TABLE 1

METHYL KETONES $$R-\overset{O}{\underset{\|}{C}}-CH_3$$

| Embodiment | R | b.p. °C., (mm Hg) |
|---|---|---|
| 6 | C(CH$_3$)$_2$CO$_2$C$_2$H$_5$ | not determined |
| 7 | C(CH$_3$)$_2$CO$_2$i-C$_3$H$_7$ | 54, (11) |

Embodiment 8

1-Bromo-3,3-dimethyl-2-pentanone

A stirred solution of 32.0 g of the methyl ketone of Embodiment 2 above in 400 ml anhydrous ether was cooled with an ice bath and treated dropwise with 14.4 ml of bromine. Immediately after addition was complete and the color had changed from dark brown to pale yellow, the reaction mixture was washed with water and brine, dried (MgSO$_4$), and stripped to give 49.16 g of a pale yellow oil. Distillation yielded 38.05 g of the desired product as a colorless oil, b.p. 48°–51° C. (0.02 mm Hg).

Embodiment 9

1-Bromo-4-chloro-3,3-dimethyl-2-butanone

A stirred solution of 7.00 g of the methyl ketone of Embodiment 4 above in 450 ml methylene chloride was treated dropwise with 8.31 g of bromine at such a rate that the color was rapidly discharged. The temperature was kept below 24° C. The crude mixture was then washed with water, brine, and dried over MgSO$_4$. After removal of solvent, the residual oil was distilled in a Kugelrohr apparatus to yield 9.42 g of the desired product.

Embodiment 10

Bromomethyl 2-methylphenyl ketone

A solution of 13.42 g of ortho-methylacetophenone in 15 ml of acetic acid was treated with 15.98 g of bromine in 15 ml acetic acid. After being kept at ca 100° C. for 90 minutes, the mixture was poured into 300 ml water and extracted with ether. Removal of solvent from the dried (MgSO$_4$) extract provided 19.70 g of residual oil, which by GLC was 75% pure. This crude product was used without further purification.

Embodiments 11–14

Following procedures similar to those described in Embodiments 8–10 above, the following bromomethyl ketones were prepared.

TABLE II

BROMOMETHYL KETONES $$R-\overset{O}{\underset{\|}{C}}-CH_2Br$$

| Embodiment | R | b.p. °C. (mm Hg) |
|---|---|---|
| 11 | 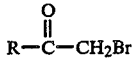 | 53 (0.5) |

TABLE II-continued

BROMOMETHYL KETONES

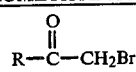

| Embodiment | R | b.p. °C. (mm Hg) |
|---|---|---|
| 12 | $C(CH_3)_2CO_2CH_3$ | 62 (0.05) |
| 13 | $C(CH_3)_2CO_2C_2H_5$ | 65–70 (10) |
| 14 | $C(CH_3)_2CO_2i\text{-}C_3H_7$ | 55–57 (0.01) |

Embodiment 15

4-(1,1-Dimethylpropyl)-1,3-thiazole-2-acetonitrile

To a solution of 10.72 g of 85% potassium hydroxide in 200 ml ethanol was added 15.56 g of 2-cyanothioacetamide of Embodiment 1 above. After stirring at ambient temperature for one hour, the reaction mixture was cooled with an ice bath, treated dropwise with 30.00 g of the bromomethyl ketone of Embodiment 8 above and stirred at ambient temperature overnight. The reaction mixture was filtered, and the solvent was removed under reduced pressure. The resulting residue dissolved in methylene chloride was passed through a florasil column to give a brown oil. Further purification by Kugelrohr distillation gave 19.74 g of the desired product as a yellow oil.

Embodiment 16

4-(1,1-Dimethylethyl)-1,3-thiazole-2-acetonitrile

To a solution of 16.5 g of 85% KOH in 250 ml ethanol was added 25.0 g of 2-cyanothioacetamide. After all of this reagent had dissolved, 44.8 g of bromopinacolone was added dropwise over ca 5 min. The reaction temperature spontaneously climbed to 65° C. and a white solid began to deposit. The mixture was stirred and heated at reflux for 1 hour, cooled, poured into 1000 ml water, and extracted with ether. The extract was washed with brine, dried (MgSO₄), and concentrated. Kugelrohr distillation of the residual oil gave 23.3 g of the desired product as a light yellow oil b.p. 90°–95° C. (1 mm Hg).

Embodiments 17–23

Following procedures similar to those described in Embodiments 15 and 16 above, the following 4-substituted-1,3-thiazole-2-acetonitriles were prepared.

TABLE III

4-SUBSTITUTED-1,3-THIAZOLE-2-ACETONITRILES

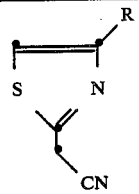

| Embodiment | R | b.p. C (mm Hg) or m.p. C |
|---|---|---|
| 17 | o-tolyl | 160–165 (0.02) |
| 18 |  | 280 (760)[a] |
| 19 | phenyl | 49–52 |
| 20 | $C(CH_3)_2CH_2Cl$ | 310 (760)[a] |
| 21 | $C(CH_3)_2CO_2CH_3$ | 310 (760)[a] |
| 22 | $C(CH_3)_2CO_2C_2H_5$ | 125 (0.05) |
| 23 | $C(CH_3)_2CO_2i\text{-}C_3H_7$ | 320 (760)[a] |

[a]This is an estimated boiling point based upon the correlation of boiling point versus Kovats index for fourteen compounds of various classes. The correlation coefficient is 0.98, and the standard error of estimate is 10.2° C. The Kovats index is obtained from a chromatographic retention time observed during gas chromatography mass spectrometry experiments.

Embodiment 24

Alpha-[Hydroxy(2,6-difluorophenyl)methylene]-4-(1,1-dimethylpropyl)-1,3-thiazole-2-acetonitrile A stirred solution of 3.5 g of the thiazole of Embodiment 15 above, 0.2 g of 4-dimethylaminopyridine and 3 ml triethylamine in 100 ml benzene at ambient temperature was treated dropwise with 3.17 g of 2,6-difluorobenzoyl chloride. The reaction mixture was stirred overnight at room temperature, diluted with methylene chloride, washed with water, dried (MgSO₄), and stripped to give 9.50 g of a brown oil. Flash chromatography with methylene chloride on silica gel, followed by trituration with ether yielded 0.43 g of the desired product as yellow crystals, m.p. 195.0°–196.5° C.

Embodiment 25

Alpha-[hydroxy(2,6-difluorophenyl)methylene]-4-(1,1-dimethylethyl)-1,3-thiazole-2-acetonitrile Acylation with Excess Acid Chloride. To a mixture of 4.0 g of the thiazole of Embodiment 16 above, 5 ml of triethylamine and 0.2 g of 4-dimethylaminopyridine in 100 ml of toluene was added dropwise 15.8 g of 2,6-difluorobenzoyl chloride. After stirring overnight at room temperature, the mixture was diluted with ether and washed with water. Removal of solvent gave a multicomponent mixture as a black oil. Chromatography on a silica gel column using hexane:ether (70:30 by volume) as eluent gave 1.8 g of a white solid identified as 2,6-difluorobenzoic acid anhydride. The column was then stripped with methylene chloride. This eluent, when stripped and triturated with ether, led to 1.0 g of the desired product as a tan powder, m.p. 207°–209° C.

Acylation with One Equivalent of Acid Chloride. A mixture of 2.0 g of the thiazole of Embodiment 16, and 2.1 ml of triethylamine in 25 ml of benzene was treated with 2.0 g of 2,6-difluorobenzoyl chloride. After stirring overnight at room temperature with exclusion of ambient atmosphere, a catalytic amount of 4-dimethylaminopyridine, 0.2 g, was added, and stirring was continued for another 24 hours. At this point the mixture was diluted to 100 ml with methylene chloride and washed with water. The organic layer was dried (MgSO₄) and concentrated. The resultant brown oil was taken up in 100 ml methanol, treated with 2 drops of concentrated H₂SO₄, and refluxed for 5 hours. When this solution was cooled and poured into 200 ml of water, the product crystallized. Filtration afforded 2.9 g of the desired product; m.p. 207°–208.5° C.

Embodiments 26–30

Following procedures similar to those described in Embodiments 24 and 25 above, the following alpha[hydroxy(2,6-difluorophenyl)methylene]-1,3-thiazole-2-acetonitriles of Formulas I, II or III were prepared.

TABLE IV 2,6-DIFLUOROBENZOYL DERIVATIVES OF
4-SUBSTITUTED-1,3-THIAZOLE-2-ACETONITRILES

| Embodiment | R | m.p., °C. |
|---|---|---|
| 26 | o-tolyl | 192–193 |
| 27 |  | 205–207 |
| 28 | phenyl | 205–207 |
| 29 | $C(CH_3)_2CH_2Cl$ | 183–186 |
| 30 | $C(CH_3)_2CO_2C_2H_5$ | >280 |

In like manner, the compounds in which R is $C(CH_3)_2CO_2CH_3$ or $C(CH_3)_2CO_2i-C_3H_7$ are prepared.

The compounds of the invention have been found to be toxic with respect to insect pests, by which is meant insects of the class Insecta and the like, especially those of the Order Lepidoptera, e.g. *Heliothis zea* (Boddie) and the like.

For application, a compound of the invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides—i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates or these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

Activity of compounds of the invention with respect to insect and acarine pests was determined by using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18-20 hours after which mortality counts were made. Both dead and moribund flies were counted. The test were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing different dosage rates for each test compound.

III. Third instar corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44-46 hours, at which time the dead and moribund larvae were counted. The tests were conducted employing several different dosage rates for each test compound.

In each set of tests, identical tests were conducted using Parathion as a standard for comparison.

In each instance, the toxicity of the test compound were compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Embodiment Number | Toxicity Index | | |
|---|---|---|---|
| | Housefly | Pea Aphid | Corn Earworm |
| 25 | + | 2 | 329 |
| 24 | 4 | 4 | 219 |
| 26 | 6 | + | 128 |
| 27 | 0 | + | 65 |
| 28 | + | 9 | 40 |
| 29 | + | 1 | 41 |
| 30 | + | 36 | 2 |

+ "means" some toxicity at the concentration tested but less than 1.

What is claimed is:
1. A compound of the formula I, II, or III

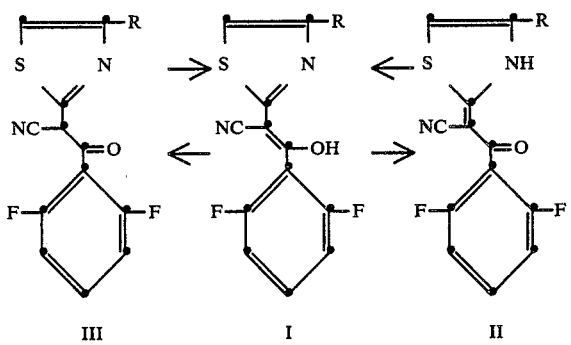

wherein R is an alkyl group containing 2 to 6 carbon atoms optionally substituted by one or more halogen atoms, a cycloalkyl group containing 3 to 6 ring carbon atoms optionally substituted by one or more alkyl groups containing 1 or 2 carbon atoms, an aryl or aralkyl group containing 6 to 10 carbon atoms optionally ring-substituted by one or more halogen atoms or alkyl groups containing 1 or 2 carbon atoms or an alkoxycarbonylalkyl group in which the alkyl portions contain from 1 to 6 carbon atoms.

2. A compound according to claim 1 wherein R is an alkyl group containing 2 to 6 carbon atoms.

3. A compound according to claim 2 wherein R is a branched-chain alkyl group.

4. A compound according to claim 3 wherein R is a tertiary-butyl group.

5. A compound according to claim 3 wherein R is a 1,1-dimethylpropyl group.

6. A compound according to claim 1 having the formula I.

7. An insecticidal composition comprising an insecticidally effective amount of a compound according to claim 1 and at least one surface-active agent or carrier.

8. A method of combatting insects at a locus which comprises applying to the insects or the locus an insecticidally effective amount of a compound according to claim 1.

9. A method according to claim 8 wherein the insects are of the Order Lepidoptera.

* * * * *